United States Patent [19]
Carson

[11] Patent Number: 4,683,295
[45] Date of Patent: Jul. 28, 1987

[54] METHOD FOR THE PREPARATION OF ANTI-RECEPTOR ANTIBODIES

[75] Inventor: Dennis A. Carson, Del Mar, Calif.

[73] Assignee: Scripps Clinic and Research Foundation, La Jolla, Calif.

[21] Appl. No.: 614,102

[22] Filed: May 24, 1984

[51] Int. Cl.$^4$ .............................................. C07K 3/08
[52] U.S. Cl. .................................... 530/391; 530/387; 530/388; 424/85; 436/547; 436/548; 435/68
[58] Field of Search ...................... 260/112 B; 424/85; 436/547; 435/68

[56] References Cited

U.S. PATENT DOCUMENTS 4,513,088  4/1985  Levy et al. ........................ 435/172.2
4,536,479  8/1985  Vander-Mallie .................... 436/819
4,545,986  10/1985 Malley ................................. 424/88

OTHER PUBLICATIONS

Strasburg, "Anti-Idiotype and Anti-Hormone Receptor Antibodies", *Springer Semin Immunopathal*, 6, 1983, pp. 67-78.

Kull et al, "Monoclonal Antibodies of Receptors for Insulin and Somatomedins-C", IBC, 258(10), 1983, pp. 6561-6566.

Couraud et al, "Immunological Statistics of P-Adrinergic Receptors", *I. Cellular Biochem*, 21, 1983, pp. 187-193.

Fraser et al, "Monoclonal Antibodies to P-Adrenergic Receptors", *PNAS*, 77(12), 1980, pp. 7034-7038.

Venter et al, "B-Adrenergic Receptor . . . Monoclonal Antibodies", *Fed Proc*, vol. 42(2), 1983, pp. 273-278.

Venter et al, "Monoclonal and Anti-Idiotypic Antibodies . . . Function", *Fed Proc*, vol. 43(10), 1984, pp. 2532-2539.

Forstrom et al, "Immunization up to a Synergies Sarcoma by Monoclonal . . . Antibody", Nature 303, 1983, pp. 627-629.

*Primary Examiner*—John Kight
*Assistant Examiner*—Garnette D. Draper
*Attorney, Agent, or Firm*—Dressler, Goldsmith, Shore, Sutker & Milnamow Ltd.

[57] ABSTRACT

A method is discussed for the production of anti-receptor antibodies and to the detection and isolation of naturally occurring anti-receptor antibodies in animals and humans. The anti-receptor antibodies can be isolated from polyvalent anti-receptor antisera by immunodepletion of anti-immunoglobulin antibodies or by a single affinity purification step using antibody raised to an antigen recognized by the receptor.

17 Claims, 7 Drawing Figures

METHOD FOR THE PREPARATION OF ANTI-RECEPTOR ANTIBODIES

TECHNICAL FIELD

The present invention relates to a method for the production of anti-receptor antibodies and to the detection and isolation of naturally occurring anti-receptor antibodies in animals and humans. The anti-receptor antibodies can be isolated from polyvalent anti-receptor antisera by immunodepletion of anti-immunoglobulin antibodies or by a single affinity purification step using antibody raised to an antigen recognized by the receptor.

BACKGROUND

Specific binding proteins (hereinafter referred to as "receptors") on the plasma membrane of a mammalian cell are essential for the interaction of the cell with the external environment. For example, receptors mediate the physiological actions of hormones, antibodies, enzymes, neorotransmitters and other biologically active substances. They are also responsible for the cellulor selectivity of drugs, toxins and poisons, and for the tissue tropism (growth response) of certain pathogenic viruses.

An antibody against a cell surface receptor (hereinafter referred to as an "anti-receptor antibody") can develop naturally in vivo, or can be induced by the deliberate immunization of a heterologous species with a purified receptor. In some cases, an anti-receptor antibody can stimulate the biological effects of a ligand or antigen recognized by the receptor. As used herein, a ligand is any substance that reacts with and binds to an antibody. An anti-receptor antibody inhibits, or reverses, the binding of a ligand to its complementary receptor without exhibiting intrinsic agonist activity.

The potential therapeutic applications of purified highly specific, anti-receptor antibodies are almost limitless. For example, the passive administration of antibodies against cellular receptors for pathogenic viruses can protect against infection by (a) binding to the viral receptor on susceptible cells and preventing virus penetration; and (b) simulating the molecular structure of the virus and inducing a specific anti-viral (anti-ligand) antibody response.

Moreover, in individuals exposed to microbial exotoxins and endotoxins, synthetic poisons, or toxic concentrations of commonly used drugs, anti-receptor antibodies can block the potential lethal pharmacologic action of the foreign agent (or antigen) by preventing its binding to cells. In some instances, a high affinity anti-receptor antibody may actually displace the toxin or drug from the receptor, thereby reversing any deleterious effects, and accelerating removal, of the toxin or drug from the body. Examples of instances in which such therapy can be life-saving include exposure to exotoxins or endotoxins, drug overdose, biological warfare, snake bite and the like.

In short, anti-receptor antibodies have a tremendous potential as therapeutic agents. However, before the present invention, such antibodies were extremely difficult and expensive to prepare. In particular, the generation of an anti-receptor antibody has heretofore required either the purification of the receptor to a condition near homogeneity, and inoculation of the essentially pure receptor into a heterologous species, and/or the screening of hybridoma antibodies derived from an animal host immunized with whole cells or semi-purified receptor preparations.

For many antigens including viruses, toxins, drugs and hormones, the specific receptors associated with the particular antigen have been well-characterized. The screening of hybridoma antibodies, however, is a time-consuming and expensive procedure. Moreover, in both instances described above, the specific anti-receptor antibody must be purified from sera or ascites (serous fluid that accumulates in the abdominal cavity). For these reasons, the development of anti-receptor antibodies for therapeutic applications has proceeded rather slowly relative to other areas of immunology.

By way of further background, an antibody is an immunoglobulin molecule that has a specific amino acid sequence by virtue of which it binds only with the antigen that induced its synthesis or with a closely related antigen. An immunoglobulin molecule includes two kinds of polypeptide chains -- a pair of larger identical polypeptide chains referred to as heavy chains and two identical smaller ones referred to as light chains. These polypeptide chains are held together by disulfide bonds and by noncovalent bonds, which are primarily hydrophobic. The heavy and light polypeptide chains are synthesized in vivo on separate ribosomes, assembled in the cell and secreted as an intact immunoglobulin molecule.

The understanding of the structure and function of immunoglobulins has been facilitated by studies of fragments produced by enzymatic cleavage of the antibody molecule. For example, treatment of an antibody molecule with the enzyme papain produces two antigen-binding fragments (designated "Fab") and a complement-binding fragment (designated "Fc"), which contains no antigen-binding capacity but determines important biological properties of the intact molecule.

Treatment of an antibody molecule with the enzyme pepsin, on the other hand, produces an antigen-binding fragment (F(ab)'$_2$) and a somewhat smaller complement-binding fragment (Fc).

The amino-terminal half of the light (L) chains and the amino-terminal quarter of the heavy (H) chains of an immunoglobulin molecule vary in their amino acid sequence and are termed the variable regions (V regions) of the polypeptide chains. Portions of the V region of one heavy and one light polypeptide chain contribute the site for antigen or ligand binding. The constant region of H chains allows their differentiation into a class or subclass and confers to the immunoglobulins certain biological properties such as the ability to activate complement, cross the placenta and bind to polymorphonuclear leukocytes or macrophages.

Five immunoglobulin classes (IgG, IgA, IgM, IgD, IgE) are recognized on the basis of structural differences of their heavy chains including the amino acid sequence and length of the polypeptide chain. The antigenic determinants on the heavy chains also permit the identification and quantitation of the immunoglobulin classes by immunochemical assay techniques.

Such immunochemical assay techniques include radioimmunoassay (RIA) which establishes a competition between a known amount of a radioactive labeled antigen and an unknown amount of the same or a similar antigen present in a biological sample with a limited, standard amount of an antibody.

Another immunochemical assay technique is enyzme immumoassay (EIA) which can be even more sensitive than RIA methods. Four basic forms of EIA have been developed; the competitive binding, or enzyme-linked immunosorbent assay (ELISA) test, the immunoenzymometric test, the sandwich method for antigen or antibody, and the homogeneous EIA.

The ELISA test was the first to be developed and is patterned after the standard competitive RIA procedure. Labeled and unlabeled antigen compete for attachment to a limited quantity of solid-phase antibody. The enzyme label that is displaced is quantitated, and the calculations that follow are essentially the same as in RIA procedures.

In the immunoenzymometric procedure, an unknown quantity of antigen is reacted with an excess of enzyme-labeled antibody, and then solid-phase antigen is added. Centrifugation removes the antibody molecules that reacted with the solid-phase antigen, leaving enzymic activity in the soluble phase. The enzyme actively associated with the soluble phase is thereafter measured, and thereby provides a measure of the antigen concentration in the unknown sample.

The sandwich technique relies on the multivalence of antigen and its capacity to bind simultaneously with two molecules of antibody. The first antibody molecule is usually a solid-phase reactant. It is used in excess to ensure binding (complexation) of all the antigen molecules in the unknown sample. After admixture of the sample to be assayed and the antigen-antibody complex-forming reaction is completed, an enzyme-labeled antibody is added and incubated with the complex resulting from the first admixture. An excess of the labeled antibody combines with the available determinants on the antigen. Excess labeled antibody is removed by washing and enzyme activity is determined. As before, the amount of enzyme bound to the complex is an indirect measure of the amount of antigen in the assayed sample.

The term "homogeneous immunoassay" can be applied to any immunoassay system in which both the immunological reaction itself, and the detection of the extent to which the immunological reaction has occurred, are carried out in homogeneous solution, that is, without the use of a physical separation of the free and antibody-bound components. Three components are usually required. Specifically, a particular antibody, a labeled antigen and a sample that contains an unknown amount of the antigen. It is necessary that the signal arising from the label is modified, directly or indirectly, upon binding to the antibody.

Labels that produce modified signals upon binding in immune complexes include free radicals [Schneider et al., "Use of Enzyme and Spin Labelling in Homogeneous Immunochemical Detection Methods, " in Immunoassays for Drugs Subject to Abuse, Mule et al., eds., 45, CRC Press, Boca Raton, Fla., (1974)]; fluorescent dyes such as fluorescein [Ullman, E. F., *Clin. Chem. (Winston-Salem)*, 24, 973 (1978)]; enzymes such as horseradish peroxidase (HRP) and glucose oxidase [Rubenstein et al., *Biochem. Biophys. Res. Comm.*, 47, 846 (1972); bacteriophages [Haimovich et al., *Isr. J. Med. Sci.*, 5, 438 (1969)]; coenzymes [Carrico et al., *Anal. Biochem.*, 72, 271 (1976)]and phospholipid vesicles [Kinsky, S.C., *Methods Enzymol.*, 328, 501 (1974)].

Homogeneous immunoassays are most often performed simply by mixing the sample with the reagents and measuring the signal produced by the label. Elimination of the step required in a radioimmunoassay of physically separating the free label from that which is bound to the antibody provides an important simplification and avoids a major source of imprecision in the assay. On the other hand, the main advantages of such extraction or separation steps, namely a reduction in the background signal and the elimination of interfering substances, is sacrificed. One clear advantage is that homogeneous immunoassays can be easily automated.

The specificity of the molecular binding site of an antibody is termed its idiotype. The term idiotype denotes the unique variable (V) region sequences produced by each type of antibody-forming cell. An antibody whose binding site specificity is for the binding site of another antibody is termed an anti-idiotype antibody and can be regarded as an immunologic marker for the antibody combining site. Thus, as used herein, an anti-idiotype antibody can be one form of anti-receptor antibody.

The term "cross-reactivity" refers to the ability of an antibody to bind antigens other than its idio-specific antigen. Cross-reactive anti-idiotype antibodies can be divided into two major groups. One group comprises those anti-idiotype antibodies that recognize antigenic determinants that are associated with specific amino acid sequences in the heavy and light chain variable regions. Anti-idiotype antibodies of this group often reflect the action of inherited immunoglobulin structural genes. Consequently, these antibodies do not cross-react in subjects that are not genetically similar.

The second group includes anti-idiotype antibodies that are of cross-reactive and anti-idiotype antibodies the "internal image" of the antigen. The antigenic site recognized by this group of anti-idiotype antibodies is not associated with a particular light or heavy chain amino acid sequence. Because the antibody binding site bears the internal image of the antigen; i.e. mimics the size, shape, change and/or van der Waals attraction of the antigen, this group of anti-idiotype antibody binds to many different antibodies of the same specificity. The idiotypes recognized by such antibodies can be produced by individuals with different genetic backgrounds and are controlled by genes that bear no special relationship. Several investigators have prepared internal image anti-idiotype antibodies.

For the most part, antibody response is directed against invading organisms and altered self cells or self antigens. For example, rheumatoid factor (RF) is an IgM or IgG antibody with specificity for the Fc fragment of IgG. Rheumatoid factor usually results from an abnormal condition and causes synovial inflamation and vascolitis. IgM-RF is abundant in the sera of most individuals with rheumatoid arthritis. IgM-RFs in rheumatoid sera are polyclonal and react with a number of different antigenic determinants in the Fc region of IgG. IgM-RF from unrelated individuals show cross-reactive idiotypes.

Several laboratory tests are now available to detect rheumatoid factor. The earliest test, now rarely used, was the streptococcal agglutination reaction.

The latex fixation test is now the most commonly used method for detecting rheumatoid factor. Aggregated gamma-globulin (Cohn Fraction II) is adsorbed onto latex particles, which agglutinate (clump) in the presence of rheumatoid factor. The latex fixation test is not specific for RF, but is very sensitive, resulting in a high incidence of false positive results.

The sensitized sheep red cell test (Rose-Waaler test) depends on specific antibody binding and is the most specific test in common use. Sheep red blood cells are coated with rabbit IgG antibody specific for sheep red blood cells, and the sensitized sheep cells agglutinate in the presence of rheumatoid factor.

More complicated tests include a radioimmunoassay for IgM rheumatoid factor and an immunodiffusion assay, the latter of which provides better quantification and more precise information on the immunoglobulin classes of rheumatoid factor.

Like any other antibody, anti-idiotype antibodies can be raised against IgM-RF. Anti-idiotype antibodies bearing the IgG-Fc internal image of RF react specifically with the majority of IgM-RF antibodies from rheumatoid arthritis patients. As previously stated, this is because the binding site is not associated with a particular light or heavy chain amino acid sequence, but rather because it resembles the internal image of the IgG Fc.

IgM-RFs are regularly induced in normal humans by polyclonal B cell activation. IgM-RF production eventually terminates following the withdrawal or elimination of the inducing stimulus. The factors responsible for sustained IgM-RF response are not yet fully understood. A network of idiotype and anti-idiotype antibodies has been hypothesized to modulate antibody response. It is believed that such a mechanism of idiotype and anti-idiotype immunomodulation may play some role in controlling the synthesis of RF antibodies.

Thus, it would be desirable to identify and characterize cross-reactive RF anti-idiotype antibodies. In order to do on this, it would be advantageous to have a simple procedure to purify RF anti-idiotype antibodies. Also, it would also be advantageous to have a general procedure for the purification of cross reactive anti-idiotype antibodies for other pathogenic auto-antibodies. Currently, no simple methods for purifying anti-idiotype antibodies are known.

The present invention, however, includes a method for the detection and purification of anti-receptor antibodies and (in a particular embodiment) anti-idiotype antibodies.

SUMMARY OF THE INVENTION

The present invention contemplates a method of preparing an anti-receptor antibody that comprises the following steps:
 (a) administering to a first animal host a receptor-containing composition in an amount sufficient to induce the production of an anti-receptor antiserum containing anti-receptor antibodies;
 (b) recovering the anti-receptor antibodies from the anti-receptor antiserum of the first animal host in partially purified form;
 (c) administering to a second animal host of the same species as the first animal host (a homologous animal) a ligand in an amount sufficient to induce the production of anti-ligand antiserum containing anti-ligand antibody, said ligand binding to said receptor;
 (d) recovering the anti-ligand antibody from the anti-ligand antiserum of the second animal host;
 (e) combining the anti-receptor antibodies and the anti-ligand antibody to form a first admixture containing a first complex;
 (f) separating the first complex from the first admixture;
 (g) decomplexing the first complex; and
 (h) isolating substantially pure anti-receptor antibody.

In a further embodiment, the method also includes the steps of:

(i) combining the substantially pure anti-receptor antibody with the receptor-containing composition of step (a) to form a second admixture containing a second complex;
 (j) separating the second complex from the second admixture; and
 (k) decomplexing the second complex and isolating a substantially pure receptor.

Moreover, the method can include the step of:
 (l) administering to a third animal host the substantially pure receptor to produce an antiserum in the animal having a greater concentration of anti-receptor antibody than the concentration of anti-receptor antibody produced according to step (a).

The receptor-containing composition mentioned above may be constituted by whole animal cells, plasma membranes prepared from whole animal cells or a heterogeneous cell preparation. In addition, the receptor present in this composition can be immunoreactive with a ligand selected from the group consisting of a virus, parasite, toxin, drug or hormone.

Another aspect of this invention includes a method of preparing an anti-receptor antibody comprising:
 (a) administering to a first animal host a receptor-containing composition in an amount sufficient to induce the production of an anti-receptor antiserum containing anti-receptor antibody;
 (b) administering to a second animal host a ligand that binds with that receptor in an amount sufficient to induce the production of anti-ligand antiserum containing anti-ligand antibody;
 (c) recovering the anti-ligand antibody from the anti-ligand antiserum of the second animal host;
 (d) coating the surface of an assay means with a predetermined amount of the anti-ligand antibody, to form a coated assay means;
 (e) contacting the coated assay means with the anti-receptor antiserum containing the anti-receptor antibody;
 (f) maintaining the contact for a predetermined period of time sufficient for the coating of the coated assay means to react with the anti-receptor antibody and deplete the antibody contained in the antiserum;
 (g) separating the depleted anti-receptor antiserum from the coated assay means; and
 (h) recovering the anti-receptor antibody from the coated assay means.

The above method can be used, for example, to mimic the structure of HLA (human leukocyte antigen) antigens [these specific binding proteins are more properly referred to as "receptors" as that term is used herein], which are difficult to purify biochemically. In operation, a mouse monoclonal antibody, for example, is injected into a second mouse to produce substantially only anti-idiotype antibodies. The anti-idiotype antibodies are believed to have the mirror image conformation of the original antibody combining site. When the anti-idiotype antibodies are then injected into a rabbit, for example, a polyclonal response having a high affinity with several antibody specificities to the original antigen can be produced.

The present invention is also particularly applicable to the production of synthetic antigen surrogates that are difficult to develop by conventional methods. One such application is in the production of red blood cell antigens that can be bonded to a support means including polystyrene beads and polyvinyl chloride microtiter wells to replace conventional red blood cell reagents.

The present invention can also be applied to the production of vaccines, specific antibodies, therapeutic agents (including anti-receptor antibodies, inhibitors and the like) and imaging agents. For example, the usefulness of specific antibodies has already been demonstrated by preventing Rh(D) sensitization in potentially subsceptible pregnant women. The administration to the mother of specific antibodies raised to D antigen (RhoGAM) within 72 hours after delivery prevents sensitization and consequently inhibits the development of erythroblastosis fetalis (hemolytic anemia of the fetus or newborn caused by the transplacental transmission of maternally formed antibody characterized by an accelerated destruction of erythrocytes and consequent jaundice) during the next pregnancy.

Moreover, because allergic individuals can develop an almost individual response to allergens, the present invention can be employed to specifically design antibodies for immunotherapeutic treatment of allergies.

Compared to currently available procedures for the preparation of anti-receptor antibodies and anti-idiotype antibodies, the present method has several advantages and benefits: (i) a purified receptor is not required; (ii) the method is relatively inexpensive, (iii) the antireceptor antibodies can be used to purify the receptor and to prepare second generation antisera in large animals, and in large quantities; and (iv) the identical procedure can be used to isolate naturally occurring anti-receptor antibodies from humans.

The potential therapeutic application of the procedure in humans is particularly relevant. The administration to humans of heterologous antibodies, even in small amounts, can produce hypersensitivity reactions. Thus, preferably, antibodies to human receptors are administered to human patients.

Anti-receptor antibodies are known to occur naturally in various autoimmune states, and may develop even in normal subject following immunization or natural exposure to viruses, parasites, toxins or drugs. The availability of the purified heterologous anti-receptor antibodies allows easy identification of humans who have antibodies with the same specificity. Appropriate subjects can then be plasmapharesed, and their anti-receptor antibodies purified to homogeneity via immunoadsorbent chromatography.

The word "homologous" is used herein in its usual sense to mean a substance from the same animal species as the species of the host. The word "autologus" is also used in its usual sense to mean a substance obtained from the same animal into which it is later introduced.

Homologous and autologous antibodies are sometimes described as "self" antibodies and are non-immunogenic in host animals. Heterologous substances, on the other hand, are obtained from a species other than that of the host into which they are introduced. Heterologous antibodies are sometimes referred to as "non-self" antibodies and are immunogenic when introduced into host animals.

Still further advantages and benefits of the present invention will become apparent to those skilled in the art from the detailed description, examples and claims which follow.

BRIEF DESCRIPTION OF THE DRAWINGS

In the drawings, which constitute a portion of this disclosure.

DETAILED DESCRIPTION OF THE INVENTION

I. Introduction

Figure 1:
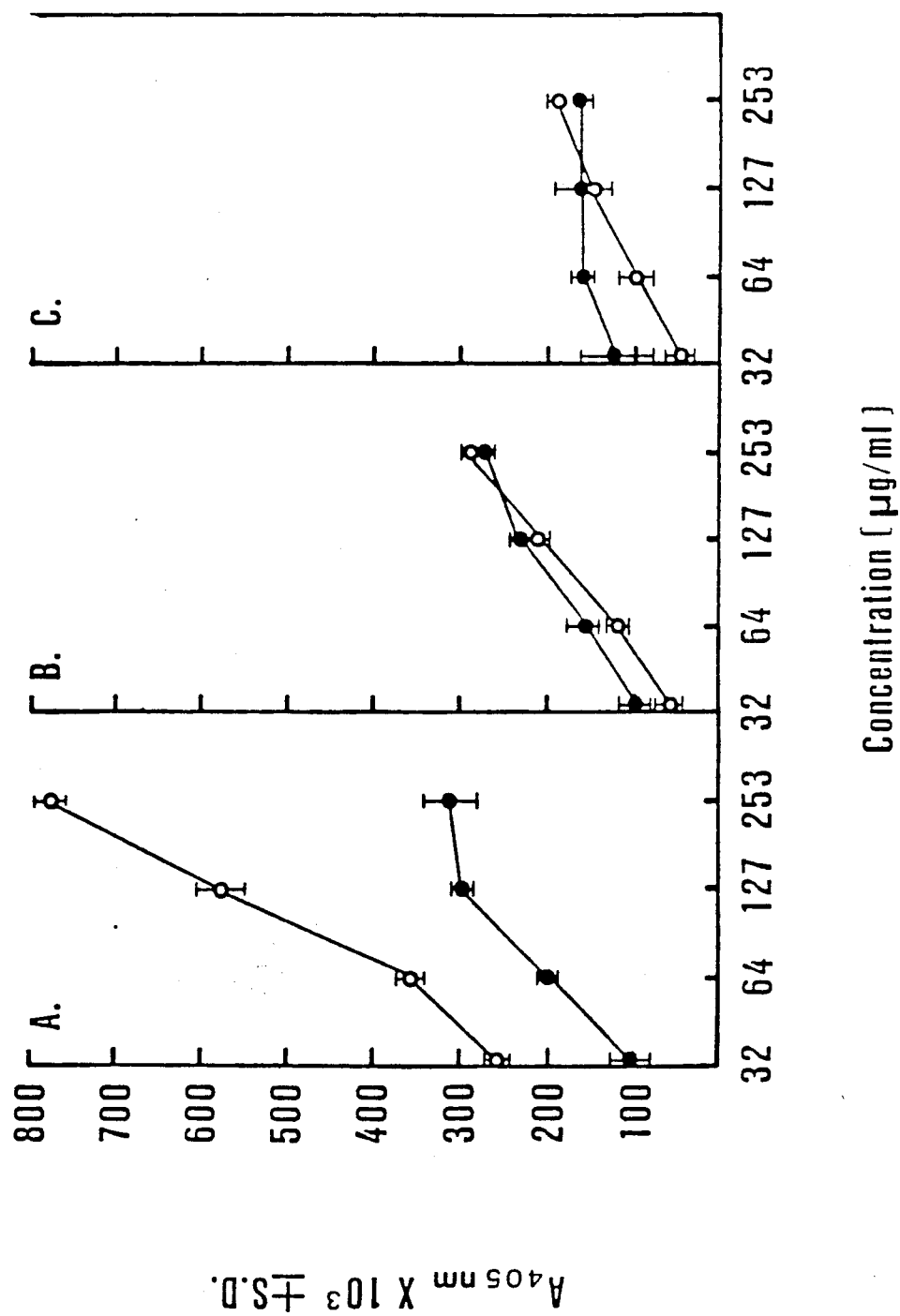
FIG. 1 illustrates the direct binding of rabbit F(ab')$_2$ anti-rheumatoid factor (RF) (open circles [o]) and normal rabbit F(ab')$_2$ immunoglobulin (darkened circles [•]) to IgM-RF of patient Mei (graph A); IgM-RF of patient Mei depleted of RF (graph B) and to IgM Mar (non-RF, graph C). The rabbit anti-RF antibodies were produced by immunization with IgM-RF derived from the rheumatoid arthritis patient Mei.

The present invention relates to a method for the preparation of purified or substantially pure antibodies (hereinafter referred to as "anti-receptor antibodies") against even poorly characterized receptors, and for the detection and isolation of naturally occurring anti-receptor antibodies in humans or animals. The application of anti-receptor antibodies for therapeutic purposes is also disclosed. The word "receptor" as used herein is meant to indicate an anti-idiotype antibody, the idiotype-containing polyamide portion of an antibody or the antibody binding portion of an antibody.

A typical procedure for the preparation of anti-receptor antibodies is generally described below in Section IV.

Antibodies can simulate the three-dimensional structure of almost any organic molecule. Thus, a minor proportion of antibodies prepared against a cell surface receptor will simulate the three-dimensional structure of the specific ligand or antigen for that receptor.

Moreover, an anti-ligand antibody, coupled to a solid phase, specifically binds the particular anti-receptor antibodies in a heterogeneous antiserum that simulate the three-dimensional structure of the ligand.

If the pure anti-ligand antibody, and the crude anti-receptor antiserum, are produced in the same species and strain of animals, homologous animals, non-specific interactions are minimized. As a result, the anti-receptor antibody can be purified in a single operation.

Specific interactions can also be reduced by using idiotype-containing polyamide portions or antibody binding portions of an immunoglobulin. Anti-idiotype antibodies or the idiotype-containing polyamide portions of antibodies are biochemically active in that they bind at least with one antigen or ligand when admixed therewith in aqueous solution, at least at physiological pH values and ionic strengths. Preferably, the receptors also bind to the ligand within a pH value range of about 5 to about 9, and at ionic strengths such as that of distilled water to that of about one molar sodium chloride.

Idiotype-containing polyamide portions of antibodies are the portions of antibodies that bind to an antigen ligand. Such portions include the Fab, Fab', and F(ab')$_2$ fragments prepared from antibodies by well-known enzymatic cleavage techniques.

The receptor molecules can be polyclonal as is the case for the antibodies raised to a whole protein molecule. The receptors can also be oligoclonal such as those that are raised to a polypeptide immunogen as is discussed in Sutcliffe et al., *Science*, 219, 660–666 (1983), and in the articles cited therein.

The receptors can also be monoclonal. Techniques for preparing monoclonal antibodies are well known. Monoclonal receptors useful in this invention can be prepared using a whole protein immunogen, as is customary, or by using a polypeptide as immunogen as described in Niman et al., *Proc. Natl. Acad. Sci. USA*, 80, 4949–4953 (1983). Monoclonal antibodies are typically obtained from hybridoma tissue cultures or from ascites fluid obtained from animals into which the hybridoma tissue was introduced.

The structure of the receptor need not be well-characterized. In fact, anti-receptor antibodies can be generated against any receptor as long as (a) specific antibodies against the ligand are available; and (b) the anti-ligand antibody and the anti-receptor antiserum are raised in the same species and strain of animal; i.e. the animals are autologous or homologus, or Fc portions of the anti-ligand antibody are absent when immunization with that antibody is carried out.

II. The Method

In particular, the method comprises (a) immunizing an animal host, such as a rabbit with whole receptor-containing cells or with a crude receptor preparation, the antiserum thus raised forming an "anti-receptor antiserum";

(b) immunizing a second, homologous, animal host of the same strain as the first rabbit with the purified antigen or ligand for the receptor, as where the receptor is a virus, toxin, drug or the like, and isolating the immunoglobulin class G fraction, this constitutes the "anti-ligand" antibody;

(c) coupling the anti-ligand antibody to a solid support, such as agarose, acrylamide or the like;

(d) contacting the anti-receptor antiserum and supported anti-ligand antibody, as by passing the anti-receptor antiserum through a column containing the anti-ligand antibody, to form a complex therebetween and washing to remove non-complexed material with a neutral buffer (a buffer having a pH value of about 6 to about 8);

(e) admixing a decoupling agent with the above-formed complex as by eluting purified anti-receptor antibody from the column with a denaturant, and separating the purified anti-receptor antibodies from the decomplexing agent as by dialyzing against a neutral buffer to form substantially purified anti-receptor antibodies.

If necessary, the anti-receptor antibody prepared as above can be used for (a) purification of the receptor for the preparation of second generation anti-receptor antibodies that are prepared similarly to those prepared above (first generation); and (b) detection and purification of human antibodies against the same receptor.

According to the present invention, an animal is hyperimmunized by multiple injections of intact cells, plasma membranes prepared from intact cells or with another purified or crude receptor preparation. The cells used for immunization should be known to include a receptor for the particular antigen or ligand; e.g., virus, parasite, toxin, drug or hormone, under investigation. Such cells can include lymphocytes, hepatic cells, nerve cells, etc. The hyperimmunized animals produce antibodies against many different immunogens of the receptor preparation such as those on the cell surface.

In addition, animals of the same species and strain are immunized with the ligand that binds with the desired receptor, e.g. purified virus, parasite, toxin, drug or hormone. Sera are collected and an IgG enriched preparation is prepared by salt fractionation, ion exchange chromatography, and in appropriate instances, by affinity chromatography on columns containing the immunizing ligands.

The partially purified antibodies against the ligand, e.g. virus, parasite, toxin, or drug, so prepared are coupled to a solid support such as agarose or acrylamide by standard procedures. An IgG enriched fraction is prepared from animals immunized with receptor bearing cells or membranes by passing a crude IgG fraction over the affinity column containing the antibody to antigen (virus, parasite, toxin or drug) to form a complex between the anti-ligand antibodies and the anti-receptor antibodies. After extensive washing with neutral buffers to remove uncomplexed material, the bound anti-receptor immunoglobulin is eluted under denaturing conditions, and dialyzed against neutral buffer to remove the decomplexing, denaturing agent to provide the purified anti-receptor antibodies in an aqueous solution.

Specificity of the purified anti-receptor antibodies so prepared can be tested via standard radioimmunoassays, by measuring the ability of the antibodies (i) to bind to cells bearing the specific receptor, but not to cells lacking the receptors (ii) to block the biological effects of the virus, parasite, toxin, drug or hormone.

The small quantities of pure anti-receptor antibodies produced by the procedure described above can be used to directly purify the receptor by affinity chromatography. The purified antibody is first coupled to a solid phase. Lysates of cells bearing a receptor are passed over the immunoabsorbent column, and material adhering to the column is isolated.

The purified receptor can be used to prepare a second generation anti-receptor antibody. The latter reagent can be purified by affinity chromatography on a column containing antibody to the antigen as described above. This second generation antibody can be obtained in high yield, and with a high degree of purity since the second generation immunogen, the purified receptor, is itself purified relative to the first used receptor immunogen.

The assay means can comprise a conventional polyvinyl microtiter tray having a plurality of wells such as that available from Dynatech of Alexandria, VA. In an additional embodiment, the assay means can include a plurality of plastic tubes or beads.

For example, the antibody or the anti-idiotype antibody can be bound to the inner surface of polystyrene tubes or the outer surface of polystyrene beads by physical adsorption. Covalent bonding of the antibody or anti-idiotype antibody to an insoluble carrier is ordinarily preferred, since this precludes dissociation of the antibody or anti-idiotype antibody from the inert carrier. Covalent coupling can be accomplished by coupling the antibody or the anti-idiotype antibody to cellulose, Sepharose (Pharmacia Fine Chemicals, Piscataway, NJ), or Sephadex (Pharmacia) or by embedding it in porous glass beads or polyacrylamide particles as the solid phase support. The cross-linked dextrans (Sephadex or Sepharose) and porous glass entrap the large antibody molecules within their matrices and yet permit the entry and exit of smaller molecules from those matrices by diffusion.

After equilibrium is reached, centrifugation separates the bound from the free ligand. Treatment of the product with mild acid solutions regenerates the antibody or anti-idiotype antibody by dissociating the antibody-ligand complex, allowing the antibody preparation to be reused.

Anti-idiotypic antibodies have been used in various systems to study both the spectrum of the immune response [Nisonoff et al., in *Immunology* 80, Fourgerau et al. (eds), Academic Press, London, 57 (1980)] and the nature of cellular receptors to antigens [Eichmann, *Adv. Immunol.*, 26, 195 (1978)]. Because idiotypic determinants can be associated with the antigen combining site [Williams et al., *Science*, 161, 379 (1968)], the idiotypic characteristics of antibodies can be used as a mirror image to define antigenic determinants of molecules which would otherwise be difficult to determine. Moreover, the demonstration of idiotypic markers on lymphocyte receptors (Eichmann, id.) suggests that anti-idiotypic (anti-receptor) antibodies can also be used for functional studies of immune recognition.

III. Diagnostic Systems

The present invention also includes a diagnostic reagent system for the quantitative assay of an inhibitor for the complex-forming reaction between an antibody and an anti-idiotype antibody to the antibody. The diagnostic reagent system comprises in separate containers, a first reagent that is either an antibody, or an anti-idiotype antibody to the antibody coupled in biologically active form to a water-insoluble, inert support means; and a second reagent that is an indicating antibody in biologically active form produced from the reaction between the anti-idiotype antibody or the antibody respectively and an indicating group.

The first and second reagents when admixed in predetermined amounts with a predetermined amount of a composition to be assayed such as serum containing a ligand to which the monoclonal antibody was raised or an inhibitor for the reaction of the antibody and the anti-idiotype antibody provides an inhibited reaction, from which the amount of inhibition can define the concentration of the inhibitor in that composition.

In this embodiment, the receptors such as anti-receptor antibodies produced according to this invention are linked to a solid support, as previously described, that is chemically inert to the antibody to be purified by those sorbants. The phrase "chemically inert" is used herein to mean that a chemical reaction between the solid support and the antibody does not occur. However, physical interactions between the solid support and the antibody such as non-specific binding can and do occur between them, although such interactions are preferably minimized.

The solid support can comprise a variety of materials such as cross-linked dextran, e.g. Sephadex G-25, -50, -100, -200 and the like available from Pharmacia Fine Chemicals of Piscataway, NJ, agarose and cross-linked agarose, e.g. Sepharose 6B, CL6B, 4B, CL4B and the like also available from Pharmacia Fine Chemicals; Bio-Gel A-0.5M, A-1.5M, A-50M and the like available from Bio-Rad Laboratories, Richmond, Calif.; or polyacrylamide beads, e.g. Bio-Gel P-2, P-30, P-100, P-300 and the like also available from Bio-Rad Laboratories. Polyacrylamide beads have the lowest tendency for non-specific binding among the above supports, but also typically have a low porosity that limits their binding capacity. The agarose and cross-linked agarose materials are preferred herein and will be used illustratively as a solid support.

The agarose support is typically activated for linking using cyanogen bromide. The activated support is then washed and linked to the receptor molecules without drying of the activated support. The support-linked receptor is then washed and is ready for use. Unreacted groups on the support can be reacted with an amine such as ethanolamine or Tris, if desired, although the reactivity of those reactive groups decays quickly.

The affinity sorbant can be used in its loose state, as in a beaker or flask, or it can be confined in a column. Prior to use, it is preferable that the affinity sorbant be washed in the buffer or other aqueous medium utilized for antibody purification to eliminate non-specifically bound proteins or those receptors that were unstably linked to the support.

Where the principal indicating group or label is an enzyme such as HRP or glucose oxidase, additional reagents are required to visualize the fact that an immune reaction has occurred and the antibody-antigen complex has formed. Such additional reagents for HRP include hydrogen peroxide and an oxidation dye precursor such as diaminobenzidine. Additional reagents useful with glucose oxidase include ABTS dye and glucose.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry.

An indicating group or label is preferably supplied along with the receptor and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

IV. Materials and Methods

A. Preparation of Immunoglobulin Class M-Rheumatoid Factor (IgM-RF), Immunoglobulin Class M (IgM) Depleted of Rheumatoid Factor (RF), and IgM Paraproteins Sera and heparin-treated plasma were obtained from normal human subjects and human subjects (patients) with rheumatoid arthritis or Sjogren's syndrome. Polyclonal and monoclonal IgM-RF proteins and serum IgM depleted of RF were purified according to the standard methods as described in Pasquali et al., *J. Clin. Invest.*, 66, 863 (1980) and Pasquali et al., *Clin. Immunol. Immunopathol.*, 21, 184 (1981).

Most of the human monoclonal IgM-RF and IgM non-RF paraproteins used in this study are described in the following publications and their properties are summarized in Table 1: Capra et al., *Adv. Immunol.*, 20, 1 (1975), Pasquali et al., *Clin. Immunol. Immunopathol.*, 21, 184 (1981), Metzger, H., *Proc. Natl. Acad. Sci. USA*, 57, 1490 (1967), Klapper et al., *Ann. Immunol. (Inst. Pasteur)*, 127c, 261 (1976), Stone, M. J., *J. Lab. Clin. Med.*, 81, 393 (1973), Andrews et al., *Proc. Natl. Acad. Sci. USA*, 78, 3799 (1981) and Kaplan et al., *Immunochemistry*, 8, 801 (1971). Pal is a IgM kappa light chain RF paraprotein isolated from an individual with cryoglobulinemia.

TABLE 1

PROPERTIES OF IgM PARAPROTEINS

| Monoclonal IgM | $V_L$ | $V_H$ | Reactivity | Reference |
|---|---|---|---|---|
| Koh | I | I | RF | 1 |
| Lay | I | III | RF | 2, 3, 4 |
| Sie | $\kappa$III | II | RF | 4, 5 |
| Pom | $\kappa$III | III | RF | 2, 4 |
| Glo | $\kappa$III | — | RF | 6 |
| Mar | $\kappa$I | I | non-RF | 1 |
| Wag | $\kappa$I | III | anti-DNP | 7 |

1. Kaplan et al., Immunochemistry, 8, 801 (1971).
2. Capra et al., Proc. Natl. Acad. Sci. USA, 71, 4032 (1974).
3. Metzger, H., Proc. Natl. Acad. Sci. USA, 57, 1490 (1967).
4. Andrews et al., Proc. Natl. Acad. Sci. USA, 78, 3799 (1981).
5. Stone, M.J., J. Lab. Clin. Med., 81, 393 (1973).
6. Capra et al., Adv. Immunol., 20, 1 (1975).
7. Ashman et al., J. Biol. Chem., 244, 3405 (1969).

B. Preparation of Rabbit anti-RF Antibody

Two adult female rabbits from the animal stock maintained at Scripps Clinic and Research Foundation, La Jolla, Calif. were immunized subcutaneously with 0.5 milligrams of purified IgM-RF (from a patient designated as "Mei") and were emulsified in 1 milliliter of complete Freund's adjuvant. On day 21, the rabbits were immunized a second time with a boost injection of 0.5 milligrams of RF in incomplete Freund's adjuvant and were boosted a third time on day 42 with 0.5 milligrams of RF in normal saline. Each rabbit was bled 5, 7 and 9 days after the second boost injection. Serum globulins from the anti-RF antiserum or from normal rabbit serum were isolated by precipitation with 40 percent saturated ammonium sulfate.

The pepsin cleaved fragments [F(ab')$_2$](idiotype-containing polyamided portions) of immunoglobulins having antigen binding capacity to RF or normal rabbit immunoglobulins were prepared from anti-RF antiserum or from normal rabbit serum, respectively, by pepsin digestion as described in Nisonoff, A., *Methods Med. Res.*, 20, 134 (1964). The F(ab')$_2$ fragments were isolated by gel filtration on Ultrogel AcA34 (LKB Instruments, Rockville, MD).

The F(ab')$_2$ fragments so prepared lacked reactivity with goat anti-rabbit papain-cleaved crystallizable fragment of an immunoglubulin (Fc) specific antiserum (Miles Laboratories, Inc., Elkhart, Indiana) as determined by direct binding with enzyme-linked immunoabsorbant assay (ELISA) and by immunodiffusion analysis. The F(ab')$_2$ anti-RF fragments were absorbed and isolated with affinity columns of agarose coupled to pooled human immunoglobulin class G (IgG) and to a human IgM paraprotein without RF as described in Pasquali et al., *J. Clin. Invest., supra*, and Pasquali et al., *Clin. Immunol. Immunopathol., supra*.

C. Preparation of Goat and Rabbit anti-Human IgG-Fc Specific Antibody

IgG-Fc fragments were prepared by the papain digestion [as described in Porter, R. R., *Biochem. J.*, 73, 119 (1959)], of purified pooled IgG (Cohn Fraction II, Sigma Chemical Co., St. Louis, MO.) or from an IgG$_1$ myeloma protein (War). The IgG Fc fragments were isolated by sequential chromatography on diethylaminoethyl cellulose (DEAE cellulose) and Ultrogel AcA34 as described in Carson et al., *Arthritis Rheum.*, 21, 438 (1978).

Anti-Fc specific antibodies were generated by injection of a goat with Fc fragments from pooled human IgG and by injection of a rabbit with Fc fragments from the IgG₁ myeloma protein. The procedure employed in the preparation anti-RF antibodies was also followed to prepare anti-Fc specific antibodies.

D. Fractionation of the F(ab')₂ anti-Idiotype Antibody on anti-Human IgG Fc Sepharose Globulins from the two anti-Fc antisera, as described above, were precipitated with 40 percent saturated ammonium sulfate and were dialyzed against phosphate buffered saline (PBS, 0.01 molar phosphate and 0.15 molar NaCl at pH 7.4). The dialyzed immunoglobulins were then coupled to cyanogen bromide activated Sepharose-4B (Pharmacia Fine Chemicals, Piscataway, NJ) according to directions supplied by the manufacturer at a ratio of 10 milligrams of protein per milliliter of Sepharose. Ten milliliters of rabbit F(ab')₂ anti-idiotype-containing polyamides (5 milligrams per milliliter in PBS) which were previously absorbed with IgG and IgM were circulated over 5 milliliters of goat anti-Fc Sepharose-4B for 2 hours at room temperature (23 degrees C) and then for overnight at 4 degrees C. The anti-Fc Sepharose-4B was then made into a column for chromatography.

The column was washed with PBS containing 0.05 percent polyoxyethylene (20) sorbitan monolaurate (TWEEN-20) until the absorbance measured at 280 nanometers was less than 0.02 absorbance units. The absorbed protein was eluted with 0.01 molar glycine-HCl (pH 2.5), neutralized to pH 7.4 with Tris-HCl (2-amino-2-(hydroxymethyl)-1-3-propanediol-hydrochloride), and then stored at minus 20 degrees C. Similarly, 10 milliliters of a globulin fraction of rabbit anti-RF antiserum (5 milligrams per milliliter) was applied directly to a 5 cubic centimeter rabbit anti-Fc-Sepharose-4B column and was eluted according to the procedure described above.

E. Enzyme Linked Immunoabsorbant Assay (ELISA) For Idiotype

The individual wells of plastic microtiter plates (No. 3590, Costar, Cambridge, Mass.) were incubated for 4 hours with 6 micrograms human IgG in 100 microliters of PBS. The wells were washed three times with borate-buffered saline (BBS, 0.01 molar borate, 0.2 molar NaCl at pH 8.0 containing 0.05 percent TWEEN 20), and were then quenched with BBS supplemented with 10 milligrams per milliliter bovine serum albumin (BBS-BSA) to block non-specific protein binding sites on the wells. RF preparations or patient sera were incubated at room temperature (23 degrees C.) for one hour with an equal volume of PBS diluted (what ratio of dilution) decomplexed, previously immunoabsorbed F(ab')₂ anti-RF antibody portion, normal F(ab')₂ IgG or affinity purified rabbit anti-idiotype.

One hundred microliter aliquots of the various mixtures were added to the IgG coated plates. After 2 hours at room temperature and 16 hours at 4 degrees C., the wells were washed 3 times with BBS and were incubated with alkaline phosphatase labeled goat anti-human IgM (Kirkegaard and Perry, Gaithersburg, MD) diluted 1:800 in PBS.

One hour later, the plates were washed 5 times with BBS and incubated with 100 microliters of 1 milligram per milliliter p-nitrophenyl phosphate in 0.05 molar sodium carbonate (pH 9.8) and 1 millimolar magnesium chloride.

Thirty minutes later, absorbance at 405 nanometers was measured in a Titertek Multiscan meter (Flow Laboratories, Rockville, MD.). The background absorbance, derived from wells that were not precoated with IgG, was automatically subtracted.

Direct binding of anti-idiotype antibodies or antibody binding portions to wells previously coated with equal amounts (2 micrograms in 100 microliters PBS) of purified IgM-RF, IgM depleted of RF, purified IgG, or immune tetanus globulin of human origin (Hyper Tet, tetanus toxoid immune globulin, Cutter Laboratories, Inc., Berkeley, Calif.) was detected using a similar procedure, except that the plates were developed with enzyme labeled monospecific goat anti-rabbit IgG (Kirkegaard and Perry, MD.).

Control experiments tested the ability of the anti-idiotype to inhibit the binding to the respective antigens, antibodies or antibody binding portions of (i) a purified IgM anti-dinitrophenyl (DNP) paraprotein designated as "Wag" as described in Ashman, R. F., *J. Biol. Chem.*, 244, 3405 (1969), (ii) sera containing IgM anti-tetanus toxoid antibodies, and (iii) sera containing IgM anti-thyroglobulin antibodies. Microtiter wells were coated with (a) 2 micrograms of either oxygen 19-labeled DNP-BSA, aluminum phosphate adsorbed tetanus toxoid (Lederle Laboratories, Pearl River, N.Y.) at a dilution of 1:80 or (b) 1 microgram thyroglobulin, each antigen being additionally diluted with PBS to a final volume of 100 microliters. The sources of antisera and preparation of these antigens are as described in Fong et al., *J. Immunol.*, 126, 910 (1981) and Welch et al., *Clin. Exp. Immunol.*, 51, 299 (1983).

The antibodies were incubated with varying dilutions of anti-idiotype and were then added to the appropriately coated plates. After washing, bound IgM was detected with alkaline phosphatase-conjugated goat anti-human IgM by ELISA as described above. In these comparative studies, the various RF, anti-tetanus toxoid antibody, anti-thyroglobulin antibody, and anti-DNP antibody samples were tested at previously determined dilutions that yielded similar initial binding activities in an ELISA assay (0.30–0.45 absorbance units at 405 nanometers).

V. Results

A. Anti-Idiotypic Activity in Anti-RF Antiserum

Rabbit anti-RF antibodies, exemplary anti-idiotype antibodies, were induced by immunization with IgM-RF derived from the rheumatoid arthritis patient Mei. After sequential adsorption on columns containing pooled human IgG, and a human IgM paraprotein without RF activity, the F(ab')₂ fragments from those antibodies were tested for direct binding to purified IgM-RF of the subject and to IgM of the subject depleted of RF, as well as being compared to an irrelevant IgM paraprotein. As shown in FIG. 1, the F(ab')₂ rabbit antibody portion was specific for IgM RF, and did not bind significantly to IgM non-RF proteins.

The anti-RF antibody recognized antigens related to the IgG binding region of RF. As determined by ELISA and as shown in panel A of FIG. 2, increasing amounts of the anti-RF progressively inhibited Mei serum IgM-RF, or purified Mei IgM-RF, from binding to human IgG. The anti-RF (253 micrograms/milliliter) did not adhere in any detectable quantity to the IgG precoat. Nor did the anti-RF interfere with the binding of the second stage antibody of the assay, alkaline phosphatase conjugated goat anti-human IgM, to plates already coated with IgM-RF.

Figure 3:
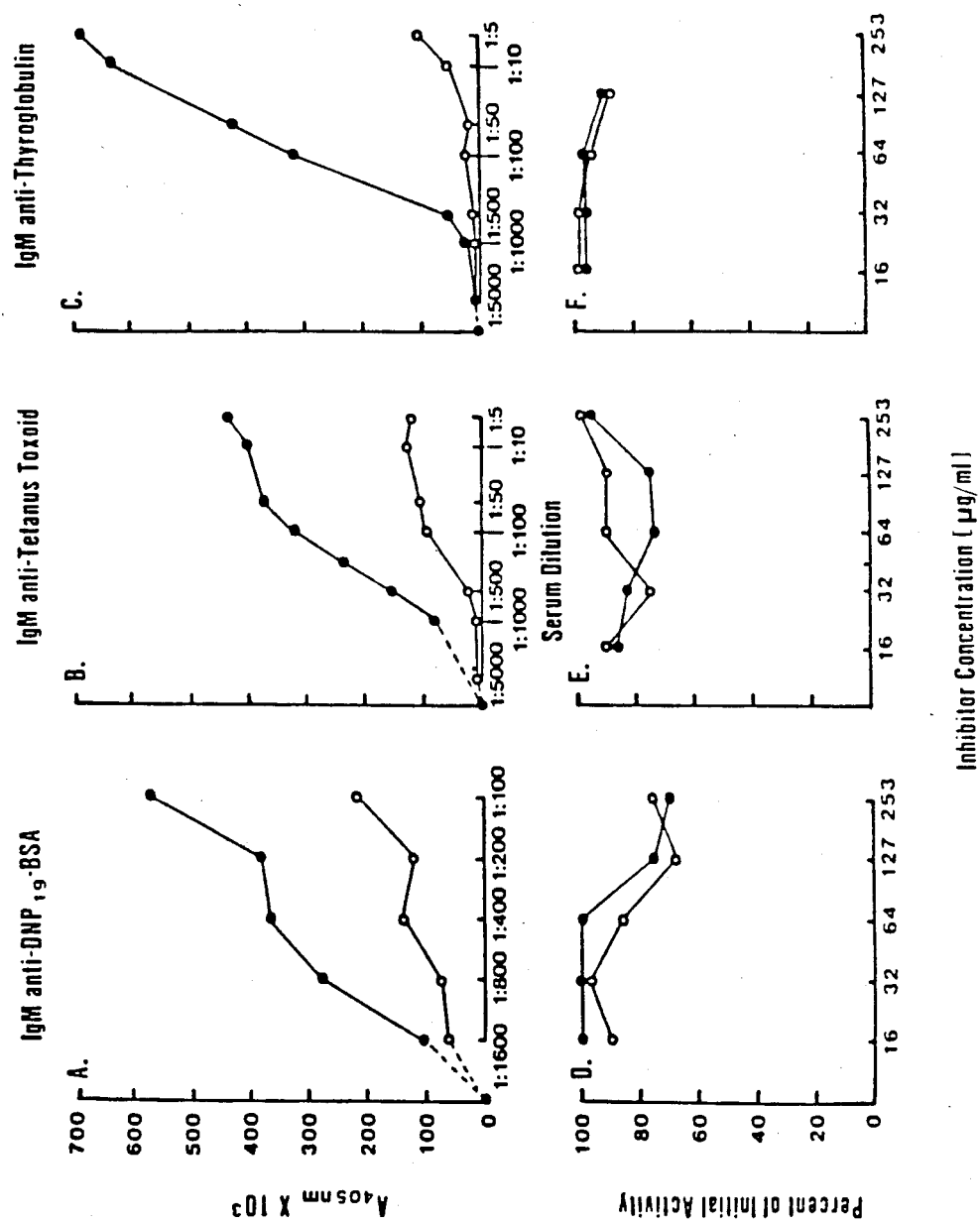
FIGS. 3A-C illustrate the direct binding to the respective antigens of IgM anti-dinitrophenyl (DNP) (graph A), IgM anti-tetanus toxoid antibody (graph B) and anti-human thyroglobulin antibody (graph C). Darkened circles (•) represent anti-antigen antibody containing serum and open circles (o) represent normal serum.
FIGS. 3D-F illustrate the ability of rabbit F(ab')$_2$ IgM-RF anti-idiotype antibody (open circles [o]) and normal rabbit F(ab')$_2$ immunoglobulin (darkened circles [•]) to inhibit the binding of the following antibodies to their respective antigen: IgM anti-DNP (graph D), IgM anti-tetanus toxoid antibody (graph E) and IgM anti-thyroglobulin antibody (graph F).

Moreover, referring to FIG. 3, rabbit anti-RF antibody did not inhibit the binding to the respective antigens of (i) the IgM anti-DNP paraprotein Wag, (ii) the IgM anti-tetanus toxoid antibody in the serum of an immunized volunteer, or (iii) the IgM anti-human thyroglobulin antibody from a patient with hypothyroidism. On the basis of these specificity controls, the anti-RF antibody was designated an anti-idiotypic reagent.

B. Reactivity of Polyclonal and Monoclonal IgM-RF Proteins with the Anti-Idiotype The sera from twelve patients with RA were tested for the presence of idiotype-positive RF by measuring the ability of the adsorbed F(ab')$_2$ anti-idiotypic antibody portion (fragment) to inhibit IgM-RF binding to IgG coated plates. The IgM-RF activity of each serum sample was titrated previously to yield an approximately equivalent activity in the ELISA procedure (0.3–0.45 absorbance units at 405 nanometers).

Figure 2:
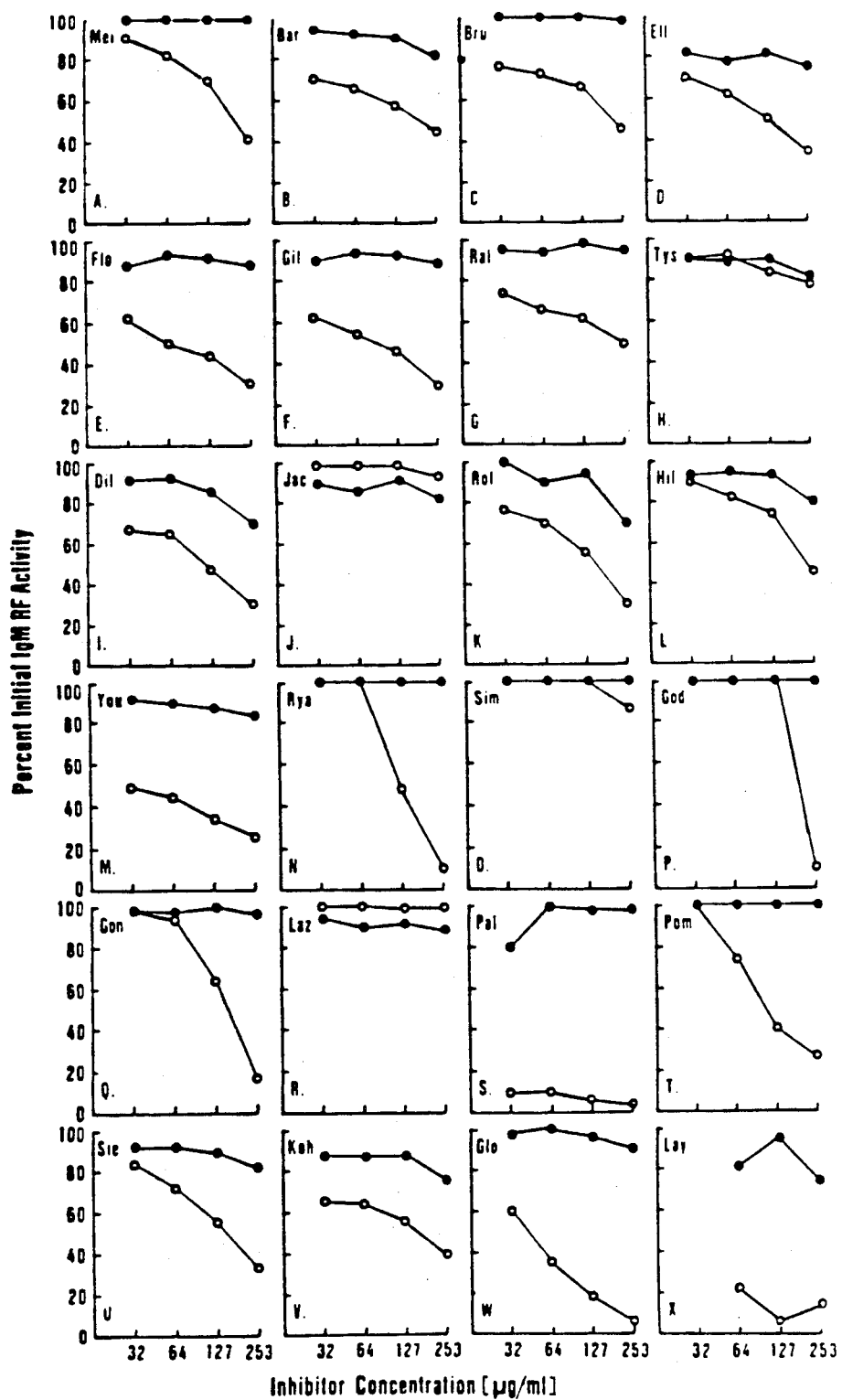
FIG. 2 illustrates the ability of rabbit F(ab')$_2$ IgM-RF anti-idiotype antibody (open circles [o]) and normal rabbit F(ab')$_2$ immunoglobulin (darkened circles [•]) to inhibit the binding to IgG by IgM-RF antibodies from plasma of patients with rhematoid arthritis (graphs A-M), Sjogren's syndrome (graphs N-R) and cryoglobunemia (graphs S-J). The designations Mei, Bar, Bro, Ell, Flo, Fl, Ral, Tys, Dil, Jac, Rul, Hil, You, Rya, Sim, G-d, Gun, Laz, Pal, Pom, Sie, Kuh, Glo, and Lay represent types of IgM-RFs from patients so designated. Data were determined by enzyme linked immunosorbant assay (ELISA) and the IgM-RF activity of each serum was previously titrated to yield an approximately equivalent activity in the ELISA (0.3 to 0.45 absorbance units at 405 nanometers).

Referring again to FIG. 2 (panels A through X), the dose-dependent inhibition of IgM-RF activity by the F(ab')$_2$ anti-idiotype antibodies or antibody binding portions, as compared to normal rabbit F(ab')$_2$ fragments is shown. The anti-idiotype antibodies or antibody binding portions significantly inhibited IgM-RF activity in the sera of 10 out of 12 patients with rheumatoid arthritis (FIG. 2, panels B-M), three out of five patients with Sjogren's syndrome (FIG. 2, panels N-R), and all of six purified monoclonal IgM-RF cryoglobulins (FIG. 2, panels S-X). Included in the latter group were the following well-characterized IgM-RF paraproteins with diverse heavy and light chain variable region subgroups, and different amino acid sequences in the complementarity determining hypervariable regions (See Table 1).

The anti-idiotype antibodies or antibody binding portions thus reacted with 83 percent of all IgM-RF preparations tested, but did not react with non-RF IgM or IgG proteins, thereby showing no false positive. This broad pattern of cross-reactivity was apparently unrelated to a particular amino acid sequence, but was associated with the antigen binding site of IgM-RF. Notably, the IgM-RF paraprotein Lay which does not bind to rabbit IgG [Metzger, H., *Proc. Natl. Acad. Sci. USA*, 57, 1490 (1967)], nonetheless reacted with the rabbit anti-idiotype antibodies or antibody binding portions. Therefore, the inhibitory activity of the anti-idiotype antibodies or antibody binding portions could not be attributed to the non-specific effects of aggregated rabbit IgG or Fc fragments. Rather the results are believed to indicate that the anti-idiotype bears the "internal image" of antigen; i.e., the Fc region of human IgG.

C. Absorption of Anti-Idiotype To Goat Anti-Human IgG Fc-Sepharose

To detect possible structural similarities between anti-idiotype-containing antibodies or binding portions thereof and antigen, the adsorbed F(ab')$_2$ anti-RF antibody portion was recirculated over a Sepharose-4B column coupled to goat antibody against human IgG Fc fragments.

Figure 4:
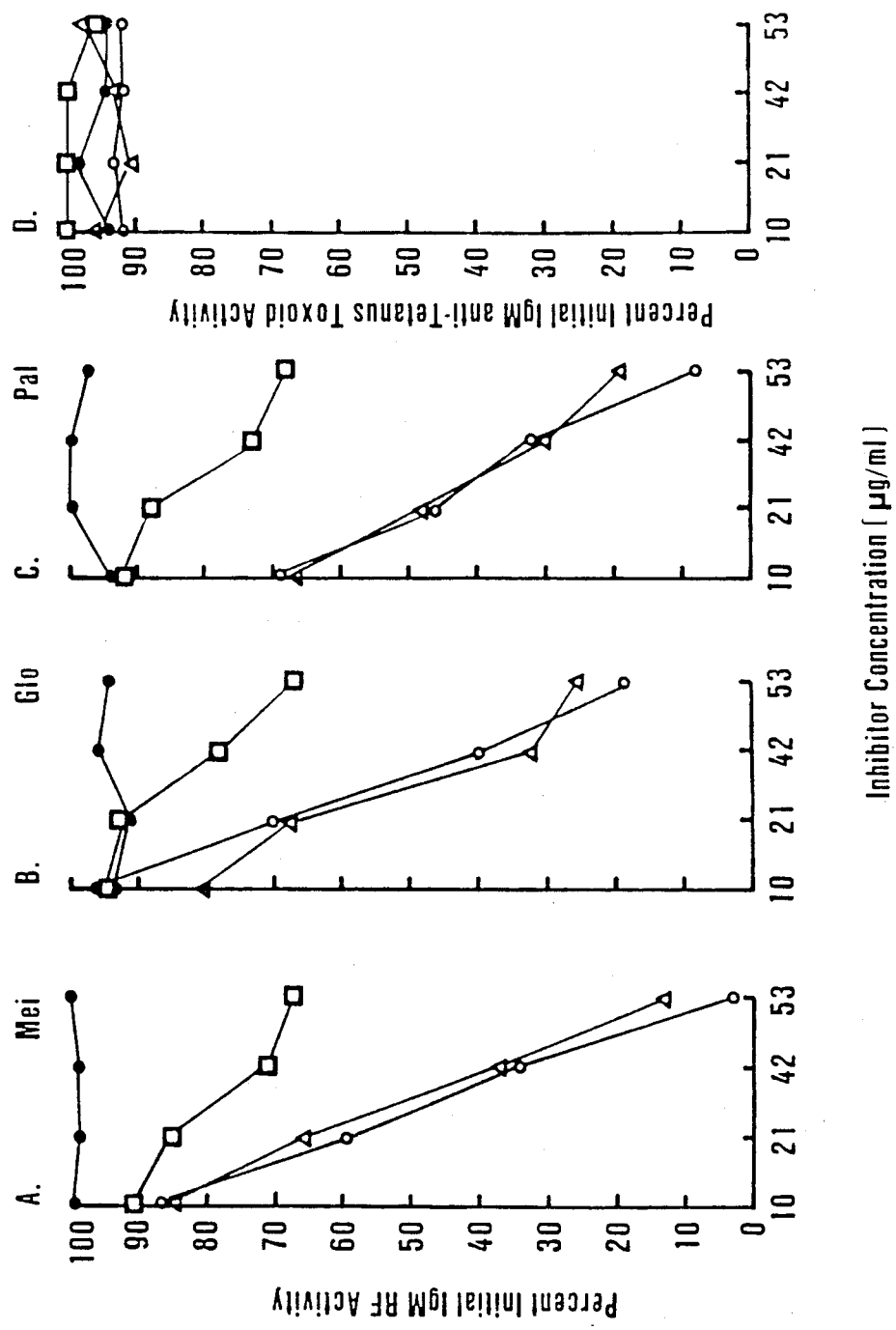
FIG. 4 illustrates the ability of the unbound fraction (square [□]) and the bound fraction (triangle [Δ]) of F(ab')$_2$ after recirculation over a Sepharose-4B column coupled to goat antibody against human IgG Fc fragments to inhibit the binding to their respective antigens of the following antibodies: IgM-RF Mei antibodies (graph A), IgM-RF Glo antibodies (graph B), IgM-RF Pal antibodies (graph C) and IgM anti-DNP protein Wag antibody (graph D). Also illustrated is the inhibition by F(ab')$_2$ anti-idiotype antibodies (open circles [o]) and normal rabbit immunoglobulin (darkened circles [•]).

As shown in FIG. 4, the unbound F(ab')$_2$ fragments were depleted significantly of anti-idiotypic activity. In contrast, the protein that bound to the column, and was eluted under denaturing conditions, reacted with the same spectrum of IgM-RF autoantibodies as the starting material, but did not react with IgM-anti-tetanus toxoid antibodies.

D. Purification of the Rabbit "Internal Image" Anti-Idiotype With Rabbit Anti-IgG Fc-Sepharose The procedure previously used for the purification of the cross-reactive rabbit anti-idiotype against human IgM-RF required the preparation of F(ab')$_2$ fragments, followed by the careful removal of contaminating antibodies with IgM and IgG affinity columns. Insufficiently adsorbed antisera lacked RF specific reactivity. Repeated adsorption with large amounts of pooled human IgG eventually depleted the antibody of cross-reactive anti-idiotypic activity.

The observation that the adsorbed rabbit F(ab')$_2$ anti-idiotype antibodies or antibody binding portions bound to a goat anti-human Fc affinity column suggested a method for the direct purification of "internal image" anti-idiotype or receptor through a single step adsorption on a homologous anti-human Fc affinity column. A rabbit anti-human Fc-Sepharose-4B column was prepared, and was incubated with a F(ab')$_2$ globulin fraction from unadsorbed rabbit anti-RF antiserum. Approximately 2 percent of the added protein bound to the column, and was eluted with glycine-HCl buffer at pH 2.5. The bound protein could then be used, as outlined in the foregoing summary of the invention section, to isolate the substantially pure receptor.

Figure 5:
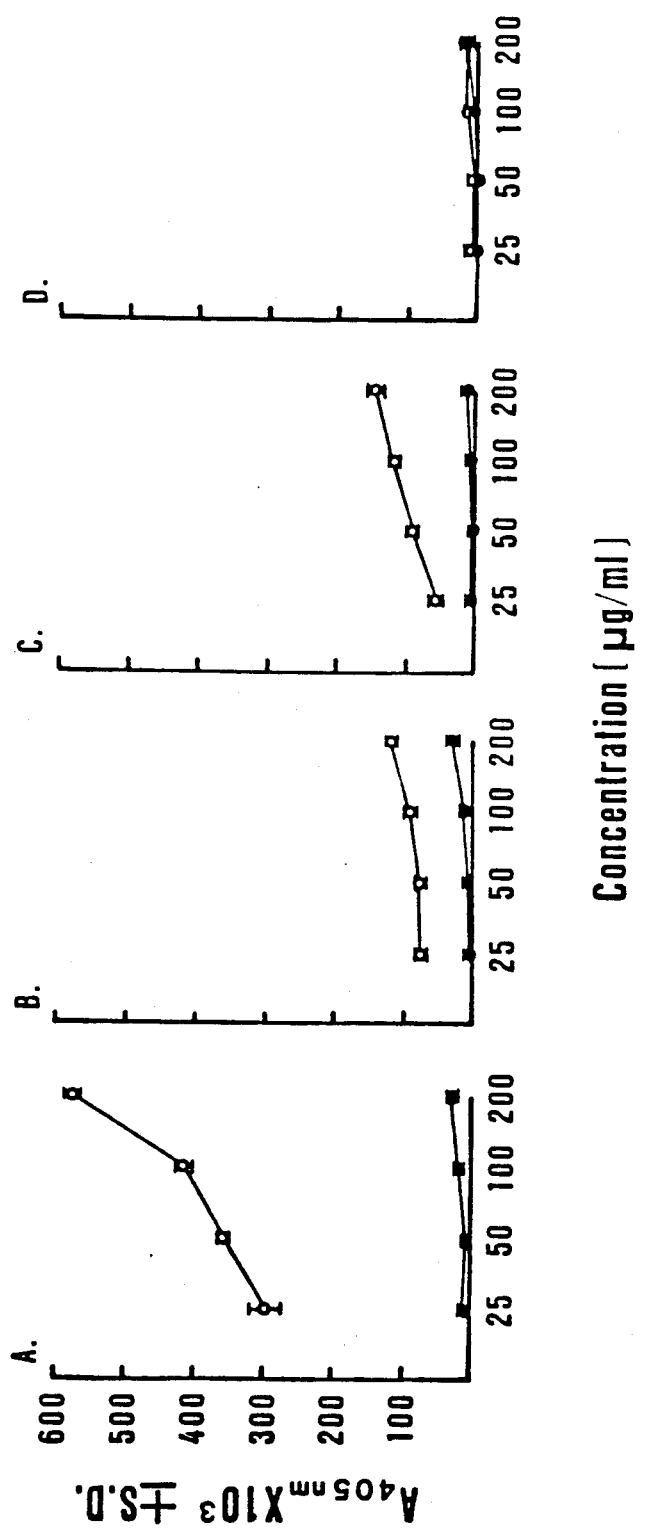
FIG. 5 illustrates the direct binding of unadsorbed F(ab')$_2$ purified by rabbit anti-human Fc-Sepharose-4B affinity chromatography (open circles [o]) and normal rabbit IgG (darkened circles [•]) to IgM-RF protein Mei (graph A), IgM of patient Mei depleted of RF (graph B), anti-tetanus toxoid (Hyper-Tet, graph C) and IgM non-RF protein Mar (graph D).

As shown in FIG. 5, the affinity-purified eluate bound to the idiotype-positive IgM-RF protein Mei, but did not bind to the Mei-RF preparation adsorbed with IgG-sepharose, hyperimmune tetanus toxoid antibodies, or idiotype negative IgM protein Mar.

Figure 6:
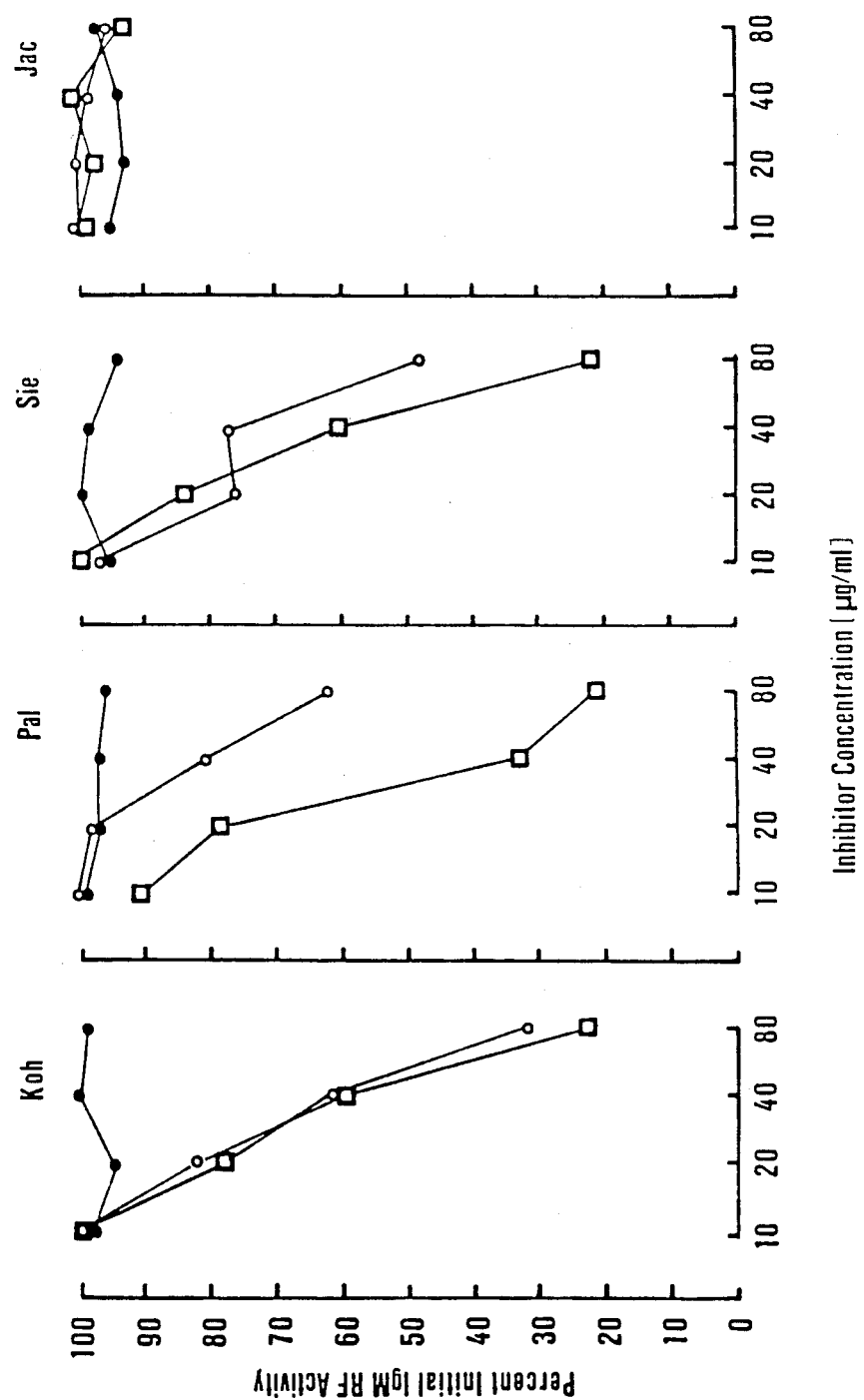
FIG. 6 illustrates the ability of RF anti-idiotype eluted from a rabbit anti-human Fc-Sepharose-4B affinity column (square [□]) to inhibit the binding to IgG by IgM-RF Koh (graph A), IgM-RF Pal (graph B), IgM-RF Sie (graph C) and IgM-RF Jac (graph D). Also illustrated is the inhibition by F(ab')$_2$ anti-idiotype prepared by immune depletion (open circle [o]) and normal rabbit immunoglobulin (darkened circle [•]). The IgM-RF activity of each serum initially ranged from 0.30 to 0.45 absorbance units at 405 nanometers times $10^3$.
Figure 7:
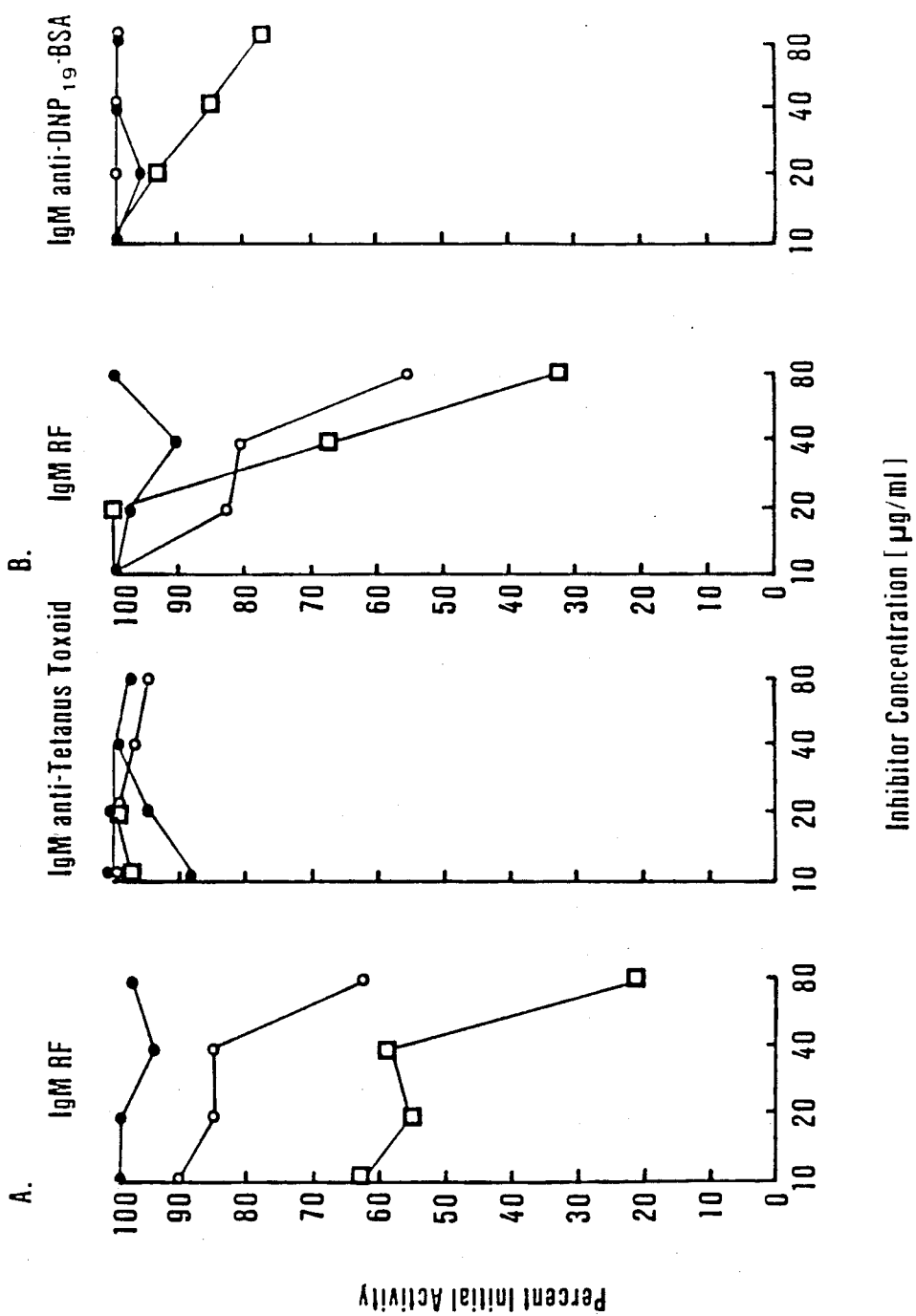
FIG. 7 illustrates the ability of rabbit anti-idiotype eluted from a rabbit anti-human Fc Sepharose-4B affinity column (open square [□]), normal rabbit IgG (darkened circle [●]) and rabbit anti-idiotype prepared by immune depletion (open circle [o]) to inhibit the binding of the following antibodies to their respective antigens; Graph A left frame: IgM-RF Mei dissolved in 1:50 dilution of anti-tetanus toxoid serum, Graph A right frame: IgM anti-tetanus toxoid serum diluted 1:50, Graph B left frame: IgM-RF Mei dissolved in a 1:200 dilution of IgM anti-DNP serum Wag and Graph B right frame: anti-DNP serum without added IgM-RF.

Similarly, the purified anti-idiotype dose-dependently inhibited the binding to IgG of four out of five IgM-RF preparations; and, indeed, as shown in FIGS. 6 and 7, exhibited the same pattern of reactivity as the anti-idiotype prepared by immune depletion techniques. In addition, the affinity-purified rabbit anti-idiotype did not inhibit the binding to antigen of IgM antibodies against tetanus toxoid or DNP and did not itself bind significantly to IgG coated plates (FIG. 7). Therefore, the anti-idiotype antibodies or antibody binding portions are not directed against $V_H$ micro framework regions, but are specific for RF.

VI. Discussion

A network of idiotypes and anti-idiotypes has been hypothesized to modulate antibody production against exogenous antigens. Idiotypic antigens on autoantibodies have been studied because of their potential use for specific immunomodulation. The present invention relates illustratively to the preparation and characterization of rabbit anti-idiotypic antibody against human IgM and anti-IgG autoantibodies (rheumatoid factors, RFs), that bear the "internal image" of the human IgG-Fc fragment, and hence react specifically with the majority of RFs from patients with rheumatoid arthritis. The illustrative examples of this invention are believed to be general of methods for the prepartion and purification of anti-idiotypic antibodies and binding portions thereof for any antigen-antibody system.

The anti-idiotype was isolated from rabbit anti-RF antisera by either immunodepletion of anti-immunoglobulin antibodies, or more simply by a single affinity purification step using a rabbit anti-human IgG Fc chromatography column. As measured by an enzyme-linked immunoassay, the anti-idiotype antibodies or antibody binding portions prepared by both methods bound to plates coated with purified IgM RF, but did not bind to plates coated with non-RF IgM proteins. The anti-idiotype antibodies or antibody binding portions dose-dependently blocked the binding to IgG or IgM-RF in 83 percent of sera from multiple patients with rheumatoid arthritis, Sjogren's syndrome and macroglobulinemia. The anti-idiotype antibodies or antibody binding portions did not inhibit the activity of human IgM antibodies against DNP, tetanus toxoid or thyroglobulin.

The antigen recognized by the cross-reactive anti-idiotype antibodies or antibody binding portions apparently was not associated with a particular light or heavy chain of the amino acid sequence, but rather was intrinsic to most immunoglobulins with RF activity. According to the present invention, broadly cross-reactive anti-idiotypes with the "internal image" of IgG are simple to generate, and react with most RFs. Moreover, these anti-idiotypes can facilitae investigations on the specific regulation of the human anti-IgG autoantibody response.

VII. Vaccine Preparation

The anti-idiotype antibodies prepared according to the present invention can be used as vaccines. Moreover, vaccine compositions other than those containing unmodified, whole anti-idiotype antibody can also be prepared. Such vaccines can be based upon (1) partially synthetic antigens or, (2) wholly synthetic antigens derived from the anti-idiotype antibodies.

A. Partially Synthetic Immunogens from Anti-idiotype Antibodies

It is known that an antibody binds to the antigen in the amino-terminus region of the antibody molecule identified as the variable region. Variable regions appear on each of the light and heavy chains of an immunoglobulin molecule such as IgG. Limited proteolysis of IgG by papain yields two fragments of the IgG molecule known as Fab and Fc, and it is the Fab protion that binds antigens.

Thus, an anti-idiotype antibody prepared according to the present invention when subjected to limited proteolysis with papain, produces Fab fragments that will bind to the original antibody from which the anti-idiotype antibody was prepared and that also mimic the immunological behavior of the original antigen. The Fab fragments can be purified from the reaction mixture by passage of the reaction mixture thorugh an immunosorbent that contains the original antibody bound to the sorbing substrate. This procedure binds the proper Fab fragments to the antibody while the remaining reaction products are swept through the column. There may be some unreacted IgG that is also bound to the column. After elution of the sorbed reaction mixture from the column, the sorbed Fab fragment are separated therefrom using conventional procedures.

The collected Fab fragments are concentrated and affixed to a carrier such as keyhole limpet hemocyanin, tetanus toxoid, curcunbin, edestin and the like, as is known in the production of synthetic antigens [see for example, Bittle et al., *Nature*, 298, 30 (1982)], or used without a carrier to produce a partially synthetic immunogen. The prepared synthetic immunogen is then combined in a suitable physiologically tolerable diluent and used as a vaccine against the original antibody or as a diagnostic reagent, as discussed in Section III.

In an alternative embodiment, the enzyme pepsin can be used instead of papain. This enzyme is known to cleave the heavy chains on the C-terminus side of the inter-H chain disulfide bonds to yield a large fragment having a molecular weight of about twice that of Fab. That large fragment is denominated F(ab')$_2$. The F(ab')$_2$ particle that is produced can be purified as described above and then used alone or bound to a suitable carrier by a technique similar to that used for the Fab fragment for the production of vaccines or diagnostics.

Use of the F(ab')$_2$ fragment rather than the Fab fragment can produce a synthetic antigen that is more active than that produced by the Fab fragment because all four of the variable regions on the light and heavy chains of the antibody are present essentially in their original configurations.

It should be noted that a whole anti-idiotype antibody could be purified by similar immunosorbing techniques and then the whole molecule could be bound to a carrier to provide the partially synthetic antigen. However, since about three quarters of the weight of the IgG comprises materials that are non-antigen specific, antibodies may well be induced to those portions that are not efficacious in production of the vaccine. In addition, adverse interspecies immunological interactions are more likely to occur where whole antibodies are utilized as immunogens.

It should also be noted that if the variable regions which comprise the amino-terminus of each of the light and heavy chains of an IgG are cleaved with specificity from the anti-idiotype antibody, the resulting fragments can be purified as previously described and made into a synthetic antigen which would have a greater portion of its weight as an immunologically active molecule.

The amount of synthetic immunogen utilized in a vaccine is that amount that is sufficient to raise a desired antibody titer in a host animal that is vaccinated. That sufficient amount is a function of a number of variables as is well known in the art. Specifically, the amount of synthetic immunogen or active ingredient in a vaccine depends on the age and weight of recipient, the particular condition to be treated, the frequency of administration and the route of administration. The dose range can be about 10 micrograms to about 500 milligrams per kilogram of body weight exclusive of the weight of any carrier. For example, as described herein, about 0.5 milligram purified IgM-RF per inoculation was used to immunize rabbits.

B. Wholly Synthetic Antigens from Anti-idiotype Antibodies

Each L chain of an IgG molecule is bonded to the H chain of that molecule by a disulfide bond. As a result, reduction of an IgG molecule with a suitable reagent for reducing disulfide bonds such as mercaptoethanol provides the whole light chain. The light chain can be purified in a manner similar to that described above in the procedure of Section (A). Light chains so prepared typically have a molecular weight of about 23,500 and contain a little over 200 amino acids. However, antigen binding occurs at only the first 110 or so amino acids from the amino-terminus and means are known to obtain the amino acid sequences of those amino-terminal amino acids. Of the amino acids at the amino-terminal, variable region, certain positions are more variable than others.

Consequently, one can obtain anti-idiotype antibodies, separate the light and heavy chains, and then perform sequence analyses on about the first 110 amino acids of the light and heavy chains. Thereafter, comparison of those sequences with other known sequences for similar regions of an antibody provides the basis for predicting which amino acids in that sequence correspond to the determinant of the original antigen. Thereafter, those sequences which are determined to correspond to the antigenic determinants can be made synthetically, affixed to a carrier, and the prepared conjugate can be used as a vaccine or as a diagnostic means.

The foregoing is intended as illustrative of the present invention but is not limiting. Numerous variations and modifications can be effected without departing from the spirit and scope of the novel concepts of the invention. It is to be understood that no limitation with respect to the specific antibodies, compositions and uses described herein is intended or should be inferred.

What is claimed is:

1. A method of preparing an anti-receptor internal image antibody comprising:

(a) administering to a first animal host a receptor-containing composition in an amount sufficient to induce the production of an anti-receptor antiserum containing anti-receptor antibodies;

(b) recovering said anti-receptor antibodies from the anti-receptor antiserum of the first animal host in partially purified form;

(c) adminstering to a second animal host of the same species as the first animal host a ligand in an amount sufficient to induce the production of anti-ligand antiserum containig anti-ligand antibody, said ligand binding to said receptor;

(d) recovering the anti-ligand antibody from the anti-ligand antiserum of the second animal host;

(e) combining the anti-receptor antibody and the anti-ligand antibody to form a first admixture containing a first complex;

(f) separating the first complex from the first admixture;

(g) decomplexing the first complex; and (h) isolating substantially pure internal image anti-receptor antibody.

2. The method according to claim 1 further including the steps of:

(i) combining the substantially pure internal image anti-receptor antibody with the receptor-containing composition of step (a) to form a second admixture containing a second complex;

(j) separating the second complex from the second admixture; and (k) decomplexing the second complex and isolating a substantially pure receptor.

3. The method according to claim 2 further including the step of:

(l) administering to a third animal host the substantially pure receptor to produce an antiserum in the third animal host having a greater concentration of anti-receptor antibody than the concentration of anti-receptor antibody produced according to step (a).

4. The method according to claim 3 wherein the third animal host has been hyperimmunized to the receptor-containing composition.

5. The method according to claim 1 wherein the receptor-containing composition comprises whole animal cells.

6. The method according to claim 1 wherein the receptor-containing composition comprises plasma membranes prepared from whole animal cells.

7. The method according to claim 1 wherein the receptor-containing composition comprises a heterogeneous cell preparation.

8. The method according to claim 1 wherein the receptor can immunoreact with a ligand selected from the group consisting of a virus, parasite, toxin, drug or hormone.

9. A method of preparing an anti-receptor internal image antibody comprising:

(a) administering to a first animal host a receptor-containing composition in an amount sufficient to induce the production of an anti-receptor antiserum containing anti-receptor antibodies;

(b) administering to a second animal host a ligand that binds with the receptor in an amount sufficient to induce the production of anti-ligand antiserum containing anti-ligand antibody;

(c) recovering said anti-ligand antibody from the anti-ligand antiserum of the second animal host;

(d) forming a coating on the surface of a solid phase support as an assay means, said coating comprising a predetermined amount of said anti-ligand antibody, to form a coated assay means;

(e) contacting said coated assay means with said anti-receptor antiserum containing said anti-receptor antibody;

(f) maintaining said contact for a predetermined period of time sufficient for the coating of said coated assay means to react with said anti-receptor antibody and deplete the anti-receptor antibody contained in the antiserum from the antiserum;

(g) separating the depleted anti-receptor antiserum from the coated assay means; and (h) recovering the anti-receptor internal image antibody from the coated assay means in substantially pure form.

10. The method according to claim 9 wherein the receptor-containing composition comprises whole animal cells.

11. The method according to claim 9 wherein the receptor-containing composition comprises plasma membranes prepared from whole animal cells.

12. The method according to claim 9 wherein the receptor-containing composition comprises a heterogeneous cell perparation.

13. The method according to claim 9 wherein the receptor can immunoreact with an ligand selected from the group consisting of a virus, parasite, toxin, drug or hormone.

14. The method in accordance with claim 9 wherein said assay means includes a microtiter tray having a plurality of wells whose surfaces are coated.

15. The method in accordance with claim 9 wherein said assay means includes a plurality of plastic beads having coated surfaces.

16. The method according to claim 1 wherein the receptor of said receptor-containing composition of step (a) is human rheumatoid factor and the ligand of said ligand-containing composition of step (c) is a human IgG Fc antibody fragment.

17. The method according to claim 9 wherein the receptor of said receptor-containing composition of step (a) is human rheumatoid factor and the ligand of step (b) is a human IgG Fc antibody fragment.

* * * * *

UNITED STATES PATENT AND TRADEMARK OFFICE
CERTIFICATE OF CORRECTION

PATENT NO. : 4,683,295

DATED : July 28, 1987

INVENTOR(S) : Dennis A. Carson

Page 1 of 2

It is certified that error appears in the above-identified patent and that said Letters Patent is hereby corrected as shown below:

Column 2, line 68, delete "immumoassay" and insert --immunoassay--

Column 4, line 48, delete "inflamation" and insert --inflammation--

Column 5, line 29, delete "on"

Column 7, line 49, delete "tne" and insert --the--
line 50, delete "autologus" and insert --autologous--

Column 8, line 13, delete "rhematoid" and insert --rheumatoid--
line 15, delete "(S-J)" and insert --S-J)--

Column 9, line 6, delete "tetnus" and insert --tetanus--

Column 14, line 4, delete "$V_{11}$" and insert --$V_H$--

UNITED STATES PATENT AND TRADEMARK OFFICE
CERTIFICATE OF CORRECTION

PATENT NO. : 4,683,295
DATED : July 28, 1987
INVENTOR(S) : Dennis A. Carson

It is certified that error appears in the above-identified patent and that said Letters Patent is hereby corrected as shown below:

Column 19, line 47, delete "thorugh" and insert --through--

Claim 1, line 13, delete "containig" and insert --containing--

Signed and Sealed this

Thirtieth Day of August, 1988

Attest:

DONALD J. QUIGG

*Attesting Officer*          *Commissioner of Patents and Trademarks*